United States Patent
Quinlin et al.

(10) Patent No.: US 7,015,334 B2
(45) Date of Patent: Mar. 21, 2006

(54) THERMALLY STABLE BOOSTER EXPLOSIVE AND PROCESS FOR MANUFACTURE

(75) Inventors: William T. Quinlin, Amarillo, TX (US); Raymond Thorpe, Amarillo, TX (US); James M. Lightfoot, Amarillo, TX (US)

(73) Assignee: BWXT Pantex, LLC, Amarillo, TX (US)

( * ) Notice: Subject to any disclaimer, the term of this patent is extended or adjusted under 35 U.S.C. 154(b) by 106 days.

(21) Appl. No.: 10/851,354

(22) Filed: May 21, 2004

(65) Prior Publication Data

US 2006/0025603 A1 Feb. 2, 2006

(51) Int. Cl.
*C07D 491/048* (2006.01)

(52) U.S. Cl. .................................... 548/421

(58) Field of Classification Search .............. None
See application file for complete search history.

(56) References Cited

U.S. PATENT DOCUMENTS

2001/0047026 A1 * 11/2001 Antane et al. ............ 514/410

* cited by examiner

*Primary Examiner*—Golam M. M. Shameem
*Assistant Examiner*—Nyeemah Grazier
(74) *Attorney, Agent, or Firm*—D. Neil LaHaye

(57) ABSTRACT

A thermally stable booster explosive and process for the manufacture of the explosive. The product explosive is 2,4,7,9-tetranitro-10H-benzo[4,5]furo[3,2-b]indole (TN-BFI). A reactant/solvent such as n-methylpyrrolidone (NMP) or dimethyl formamide (DMF) is made slightly basic. The solution is heated to reduce the water content. The solution is cooled and hexanitrostilbene is added. The solution is heated to a predetermined temperature for a specific time period, cooled, and the product is collected by filtration.

7 Claims, No Drawings

THERMALLY STABLE BOOSTER EXPLOSIVE AND PROCESS FOR MANUFACTURE

BACKGROUND OF THE INVENTION

1. Field of the Invention

The invention is generally related to organic nitroaromatics, and more specifically to a thermally stable booster explosive and process for manufacture of the explosive.

2. General Background

A booster explosive is a material with sensitivity intermediate between a primary explosive and a main-charge explosive. It is used to transmit and augment the detonation reaction of the primary. The thermal stability is important because of their use in areas where high temperatures are encountered.

Hexanitrostilbene, an organic nitroaromatic abbreviated as HNS and also called hexanitrodiphenylethylene, is a heat resistant explosive that is commonly used in deep well charges found in the oil field or in applications requiring the explosive to withstand significant temperatures before initiation. The chemical formula is $C_6H_2(NO_2)_3$. HNS is made in type I and type II and grades A and B. The difference between type I and type II is primarily the particle size. The particle size of type I is 1–5 microns. The particle size of type II is 100–300 microns. HNS has a uniquely small critical diameter of 0.020 inch. It is relatively insensitive to heat, spark, impact, and friction, yet it finds wide use as a heat resistant booster charge for military applications.

Known booster explosives such as 2,4,6-trinitro-N-methylaniline, tetryl have certain shortcomings such as less than desirable thermal stability.

SUMMARY OF THE INVENTION

The invention addresses the shortcomings in the known art. What is provided is a thermally stable booster explosive and process for the manufacture of the explosive. The product explosive is 2,4,7,9-tetranitro-10H-benzo[4,5]furo[3,2-b]indole (TNBFI). A reactant/solvent such as n-methylpyrrolidone (NMP) or dimethyl formamide (DMF) is made slightly basic. The solution is heated to reduce the water content. The solution is cooled and hexanitrostilbene is added. The solution is heated to a predetermined temperature for a specific time period, cooled, and the product is collected by filtration.

DETAILED DESCRIPTION OF THE PREFERRED EMBODIMENT

The invention is directed to the product explosive of 2,4,7,9-tetranitro-10H-benzo[4,5]furo[3,2-b]indole (TNBFI) and a process for the manufacture of the product explosive.

The physical properties of TNBFI are as follows. The normal physical state is a solid with the appearance of orange crystals. The composition is 43.20% carbon, 1.81% hydrogen, 17.99% nitrogen, and 36.99% oxygen. The molecular weight is 387.22. The theoretical maximum density is 1.65 grams per cubic centimeter.

The thermal properties of TNBFI are as follows. Endotherm temperature is 406 degrees Celsius. Exotherm temperature is 412 degrees Celsius. Heat of combustion is 20195 Joules per gram or $1.57 \times 10^7$ Joules per mole. The vacuum thermal stability is 0.25 ml per gram, based on forty-eight hours at 200 degrees Celsius.

Sensitivity testing showed the following results. For a Type 12A Tools Drop Hammer: HF50-241 centimeters. The BAM Friction Threshold Sensitivity is greater than 36 kilograms. The product explosive is insensitive to spark gap.

Two suitable processes have been determined for manufacturing the product explosive of TNBFI. One process uses n-methylpyrrolidone (NMP) as the reactant/solvent. Another process uses dimethyl formamide (DMF) as the reactant/solvent. Generally, the reaction involves dissolving HNS in approximately ten times its mass of a reactant/solvent to which a small amount of an aqueous potassium hydroxide solution has been added.

In the process using n-methylpyrrolidone (NMP) as the reactant/solvent, an aqueous solution made up of 0.5273 grams of potassium hydroxide dissolved in 10 ml of water is mixed in approximately 20 ml of NMP. The solution is heated to approximately 100 degrees Celsius for approximately one hundred twenty minutes to reduce the water content to approximately 0.05%. The solution is then cooled to under 55 degrees Celsius and 2 grams of HNS is added. The resulting solution is then heated to 100 degrees Celsius for approximately thirty minutes and then cooled to ambient temperature. The product is then collected by filtration. Any normal filter paper is suitable.

In the process using dimethyl formamide (DMF) as the reactant/solvent, an aqueous solution of 1.2502 grams of potassium hydroxide dissolved in 1.5 ml of water is mixed in 50 ml of DMF. The solution is then heated to approximately 100 degrees Celsius for approximately sixty minutes to reduce the water content to approximately 0.05%. The solution is then cooled to under 55 degrees Celsius and 5.0047 grams of HNS is added. The resulting solution is then heated to 80 degrees Celsius for approximately thirty minutes and then cooled to ambient temperature. The product is then collected by filtration. Any normal filter paper is suitable.

The processes described above are examples that use specific volumes. In more general terms, the general mixtures of chemicals are as follows. The mixture of reactant/solvent and aqueous potassium hydroxide solution must be basic. The HNS is dissolved in approximately ten times its mass of the reactant/solvent.

Both processes are suitable for manufacturing TNBFI.

Because many varying and differing embodiments may be made within the scope of the inventive concept herein taught and because many modifications may be made in the embodiment herein detailed in accordance with the descriptive requirement of the law, it is to be understood that the details herein are to be interpreted as illustrative and not in a limiting sense.

What is claimed is:

1. A process for the manufacture of 2,4,7,9-tetranitro-10H-benzo[4,5]furo[3,2]indole, comprising the steps:
   a. mixing an aqueous solution of potassium hydroxide with dimethyl formamide;
   b. heating the mixture to a temperature of approximately 100 degrees Celsius;
   c. cooling the heated solution to under 55 degrees Celsius;
   d. mixing hexanitrostilbene in the cooled solution;
   e. heating the mixture to approximately 100 degrees Celsius;
   f. cooling the solution to ambient temperature; and
   g. collecting the product using filtration.

2. The process of claim 1, wherein the amount of aqueous potassium hydroxide is sufficient to provide a mixture with a basic ph.

3. The process of claim 1, wherein the step of heating the mixture of potassium hydroxide and dimethyl formamide is held for a time period sufficient to reduce the water content to approximately 0.05 percent.

4. The process of claim 1, wherein the amount of hexanitrostilbene is approximately one tenth of the mass of the mixture of dimethyl formamide and potassium hydroxide.

5. The process of claim 1, wherein step e. of heating the mixture is held for approximately thirty minutes.

6. A process for the manufacture of 2,4,7,9-tetranitro-10H-benzo[4,5]furo[3,2]indole, comprising the steps:
   a. mixing an aqueous solution of potassium hydroxide with dimethyl formamide to provide a mixture with a basic pH;
   b. heating the mixture to a temperature of approximately 100 degrees Celsius for a time period sufficient to reduce the water content to approximately 0.05 percent;
   c. cooling the heated solution to under 55 degrees Celsius;
   d. mixing hexanitrostilbene in the cooled solution, with the amount of hexanitrostilbene being approximately one tenth of the mass of the solution of dimethyl formamide and potassium hydroxide;
   e. heating the mixture to approximately 100 degrees Celsius for approximately thirty minutes;
   f. cooling the solution to ambient temperature; and
   g. collecting the product by filtration.

7. A process for the manufacture of of 2,4,7,9-tetranitro-10H-benzo[4,5]furo[3,2]indole, comprising the steps:
   a. mixing an aqueous solution of potassium hydroxide with n-methylpyrrolidone to provide a mixture with a basic pH;
   b. heating the mixture to a temperature of approximately 100 degrees Celsius for a time period sufficient to reduce the water content to approximately 0.05 percent;
   c. cooling the heated solution to under 55 degrees Celsius;
   d. mixing hexanitrostilbene in the cooled solution, with the amount of hexanitrostilbene being approximately one tenth of the mass of the solution of dimethyl formamide and potassium hydroxide;
   e. heating the mixture to approximately 100 degrees Celsius for approximately thirty minutes;
   f. cooling the solution to ambient temperature; and
   g. collecting the product by filtration.

* * * * *